United States Patent
Dall

(12)
(10) Patent No.: US 6,238,126 B1
(45) Date of Patent: May 29, 2001

(54) HIP COMPRESSION SCREW ASSEMBLIES AND JOINTS THEREFOR

(76) Inventor: Vagn Erik Dall, 36 Bray Bank, Old Mill Lane, Bray Maidenhead, Berkshire (GB), SL6 2BG ( * ) Notice: Subject to any disclaimer, the term of this patent is extended or adjusted under 35 U.S.C. 154(b) by 0 days.

(21) Appl. No.: 09/214,324

(22) PCT Filed: Jul. 3, 1997

(86) PCT No.: PCT/GB97/01784

§ 371 Date: Apr. 26, 1999

§ 102(e) Date: Apr. 26, 1999

(87) PCT Pub. No.: WO98/01078

PCT Pub. Date: Jan. 15, 1998

(30) Foreign Application Priority Data

Jul. 4, 1996 (GB) .................................................. 9613994

(51) Int. Cl.[7] .................................................. A61B 17/58
(52) U.S. Cl. ........................... 403/114; 403/122; 606/65; 606/66; 606/67; 606/68
(58) Field of Search .................................... 403/122, 123, 403/124, 125, 140, 56, 59, 113, 114, 115, 116, 117, 220, 221; 606/65, 66, 67, 60

(56) References Cited

U.S. PATENT DOCUMENTS

| | | |
|---|---|---|
| 1,789,060 * | 1/1931 | Weisenbach . |
| 2,918,338 * | 12/1959 | Grad ........................................ 403/56 |
| 3,437,059 * | 4/1969 | Stonier et al. ........................ 403/220 |
| 3,550,668 | 12/1970 | Coyle . |
| 4,652,166 * | 3/1987 | Gautron ............................. 403/56 X |
| 5,167,664 | 12/1992 | Hodorek . |
| 5,514,138 * | 5/1996 | McCarthy ............................... 606/65 |
| 5,642,956 * | 7/1997 | Hale ..................................... 403/122 |
| 5,807,010 * | 9/1998 | Parker et al. ..................... 403/116 X |

FOREIGN PATENT DOCUMENTS

WO 93/22982 * 11/1993 (WO) .
WO 95/11632 * 5/1995 (WO) .
WO 95/33931 12/1995 (WO) .

* cited by examiner

*Primary Examiner*—Lynne H. Browne
*Assistant Examiner*—John R. Cottingham
(74) *Attorney, Agent, or Firm*—Wallenstein & Wagner, Ltd.

(57) ABSTRACT

An adjustable two-dimensional joint for use in hip compression screw assemblies, allows for relative alignment of the lag screw and angle plate, even when these components are effectively fitted to the respective bone sections. The joint has first and second elements (2, 4), formed with complementary male and female cylindrical surfaces (10, 12), which define the plane of adjustment. The first element (2) also defines a hinge point (6) at the axis of the male cylindrical surface (10), and the second element (4) includes a fulcrum (8) extending to the axis of the female cylindrical surface (12). A setting device (20) extends between the two elements (2, 4), which can be extended or contracted to alter the angle subtended at the hinge point/fulcrum (6, 8).

8 Claims, 1 Drawing Sheet

HIP COMPRESSION SCREW ASSEMBLIES AND JOINTS THEREFOR

Figure 1:
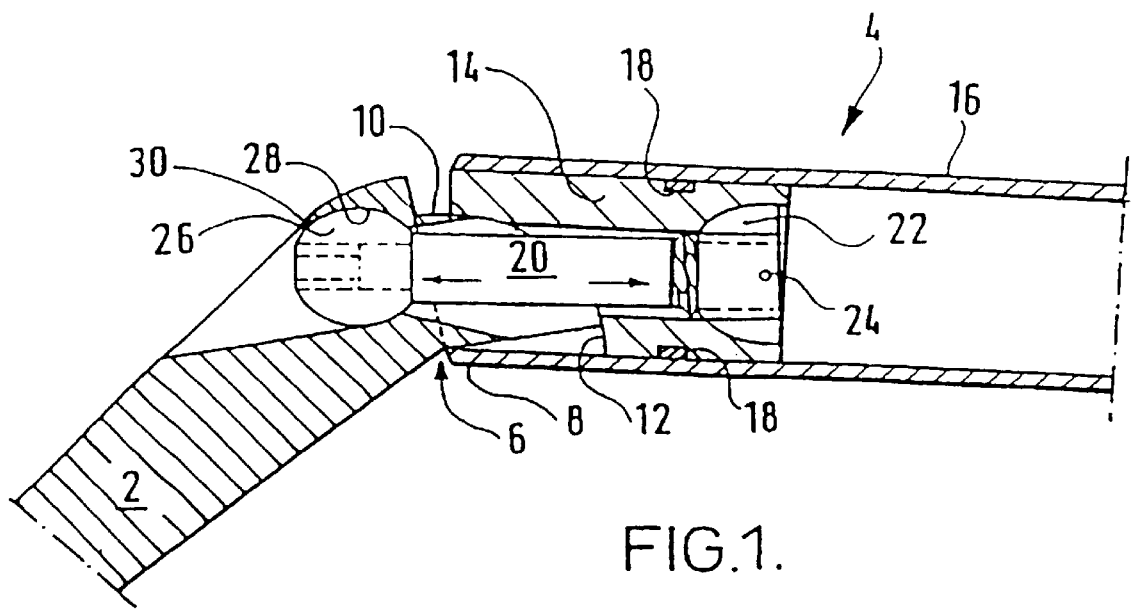

This invention relates to two-dimensional joints and their use in compression screw assemblies, particularly for use in surgical operations and in the treatment of proximal femur fracture.

In the treatment of proximal femur fracture the typical orthopaedic surgical process is to secure the fractured bone using a compression screw consisting of a lag screw and an angle plate secured thereto at a fixed angle. Such screws are available with different angles between the lag screw and plate, typically increasing at 5° intervals from 120° to 150°. The angle plates are coupled to the lag screw by a system which allows axial movement of the plate relative to the screw. Because the location of the lag screw in the treatment of a fracture of this kind is critical, the limitation on the angular relationship between the lag screw and the angle plate means that it is difficult in almost every case to fit the compression screw at the ideal position.

The present invention addresses the above problem, and provides an adjustable two-dimensional joint for use in compression screw assemblies, and which allows for relative alignment of the angle plate of such an assembly with the lag screw, even when these components are effectively fitted to the respective bone sections. A joint according to the invention, adjustable in two dimensions, comprises first and second elements formed with complementary male and female cylindrical surfaces defining the plane of adjustment, the first element defining a hinge point at the axis of the male cylindrical surface, and the second element including a fulcrum extending to the axis of the female cylindrical surface. A setting device extends between pivot points on the first and second elements which is adjustable in length between the pivot points to alter the angle between the elements. In a hip compression screw assembly, the first element will constitute or be effectively part of the angle plate and the second element constitute or be part of the lag screw.

The setting device can be located within the overall construction of a joint according to the invention, and extend along a path traversing the complementary cylindrical surfaces on the respective elements. Such a device is received in slots extending across the cylindrical surfaces in the plane of adjustment of a joint, but even with this discontinuance, there is still ample cylindrical surface on each element to allow for smooth and accurate adjustment. The preferred setting device comprises a locking screw extending from the pivot point in one of the elements, and received in a threaded sleeve extending from a pivot point on the other of the elements. One of the screw or sleeve is rotatably mounted at its respective pivot points to enable its rotation relative to the other to adjust its overall length. In this orientation, the setting device must be extended to reduce the obtuse angle between the elements, and shortened to increase the angle. As noted above, a typical range of angles in a hip compression screw assembly is 120° to 150°, and a joint of the present invention can be made infinitely adjustable within a chosen range. However, to provide for maximum flexibility in adjustment, the respective pivot points must be fixed relative to their respective elements, and for this purpose, spherical joints are typically used. Movement is normally restricted to two dimensions at one end, but rotational movement allowed at the other to enable the spacing therebetween to be varied.

A joint according to the invention is typically formed with the second element comprising a block defining the female cylindrical surface, and a sleeve surrounding the block and defining the fulcrum. This construction is particularly suited to use of the joint in a hip compression screw assembly, as the sleeve can be located in the caput, and the block fitted to the sleeve thereafter, and after coupling thereto of the setting device component or components. Provision is made for securing the block in the sleeve to ensure that the fulcrum is properly located at the axis of the cylindrical surface, and suitable locating and securing mechanisms are provided for this purpose.

Figure 2:
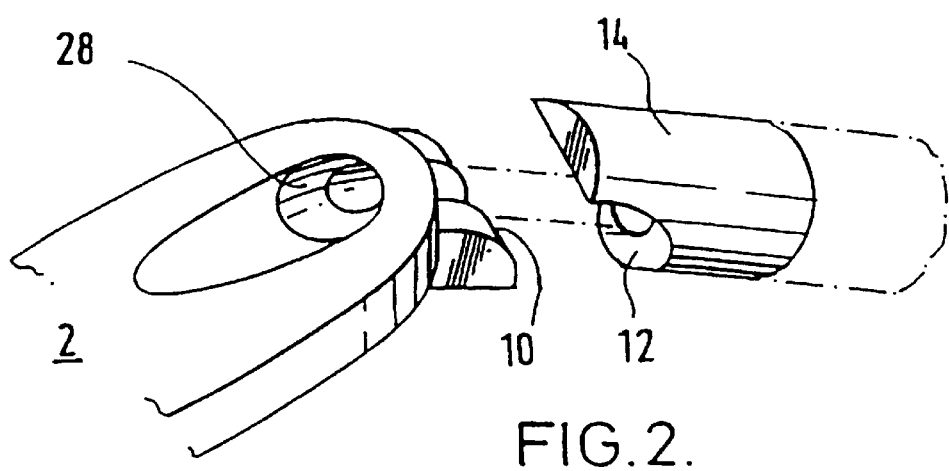

An embodiment of the invention will now be described by way of example and with reference to the accompanying schematic drawing wherein:

FIG. 1 shows in cross-section a two-dimensional joint according to the invention for use in a hip compression screw assembly; and FIG. 2 is an exploded perspective view showing the principle elements of the joint of FIG. 1.

The joint shown in the drawing has first and second elements 2, 4 which are pivotal relative to each other around a hinge point or groove 6 defined by element 2, and which receives a fulcrum 8 formed on element 4. Such pivotal movement is constrained to be in a single two-dimensional plane by complementary male (10) and female (12) cylindrical surfaces respectfully on the elements 2 and 4. The hinge point or groove 6 is located at the axis of the male cylindrical surface 10, and the fulcrum 8 at the axis of the female surface 12. The cylindrical surfaces 10, 12 are therefore in sliding engagement with each other when the fulcrum 8 is properly received in the hinge point or groove 6.

The female cylindrical surface 12 is formed on a block 14 received in a sleeve 16, the block and sleeve each being part of the element 4 which, in a hip screw assembly would constitute the lag screw secured or to be secured in the caput of a femur in the treatment of a typical proximal femur fracture. The use of a block 14 and a sleeve 16 serves a number of purposes. Primarily it enables the joint to be substantially assembled with the block 14 prior to insertion of the block 14 into the sleeve 16. Additionally though, this construction allows the sleeve 16 to be separately secured in the caput before the block 14 is located in it, and of course the location of the block 14 in the sleeve 16 can itself include a measure of adjustment to ensure that the fulcrum 8 is properly located at the axis of the female cylindrical surface 12, and coincident upon assembly with the axis of the male cylindrical surface 10. Suitable locking mechanisms 18 are provided to secure the block 14 in the sleeve 16.

To complete the adjustable joint, and enable it to be set at a chosen angle, a setting device 20 extends between the two elements 2, 4, which can be extended or contracted to alter the angle subtended at the hinge point/fulcrum 6, 8. The setting device comprises a threaded bolt extending from a spherical joint 22 in the element 4, which is constrained by two pins 24 to pivotal movement in the plane of the two elements, and a complementary threaded sleeve extending from a spherical joint 26 in the element 2. However, the spherical joint 26 does not have any constraining mechanism, and particularly the ball itself can be rotated to extend or contract the device between the respective spherical joints. The socket 28 for the spherical joint 26 is fitted with a locking device 30 to prevent the ball and sleeve from withdrawal upon extension of the setting device.

The bolt and sleeve of the setting device extend to engage each other within a slot which is formed in both elements 2, 4 where they form the respective cylindrical surfaces. This slot is better shown in FIG. 2, where it will also be recognised that ample cylindrical surface area remains to ensure that adjustment of the joint is smooth.

In the use of a joint according to the invention in a hip compression screw assembly, the sleeve 16 will be installed in the caput of the femur as a separate exercise, with the fulcrum 8 being located at the remaining bone surface. If the joint has not already been assembled, then the block 14 is offered up to the element 2, engaging the cylindrical surfaces 10 and 12. The components of the setting device are then installed, the screw or bolt normally first being located and pinned in the block, and the sleeve screwed thereonto through the slots. Seated in the socket, the ball of the sleeve is locked therein by the mechanism 30.

With the joint of the invention in loose assembly, the block is inserted into the sleeve 16 already located in the femur, and adjusted therein until the cylindrical surfaces 10 and 12 are properly engaged, and the hinge point or groove 6 properly engaged with the fulcrum 8 of the sleeve 16, when the block is secured. The sleeve 16 is then rotated to extend or contract the setting device until the element 2, in this context now forming the angle plate of the compression screw assembly, properly engages the femur surface. At this point the joint is essentially locked, and the element 2 or angle plate can be secured to the femur upon which it rests, by means for example of cortical bone screws.

While the invention has been described above specifically in the context of a hip compression screw assembly, or as a device for accomplishing the internal fixation of limbs, it should be noted that it can also be used in the external fixation of limbs. Respective bone sections can be coupled by appropriate bone screws to components which are themselves coupled by means of a joint according to the invention. The joint will allow individual adjustment to alter the relative orientation of the bone sections to be fixed.

What is claimed is:

1. An adjustable joint, comprising first and second elements formed with complementary male and female cylindrical surfaces defining a plane of adjustment, the first element defining a hinge point at the axis of the male cylindrical surface and the second element including a fulcrum extending to the axis of the female cylindrical surface, and a setting device extending between pivot points on the first and second elements and adjustable in length to alter the angle between the elements; and, wherein the adjustable joint is constrained to pivotal movement in a single two-dimensional plane.

2. A joint according to claim 1 wherein the setting device (20) extends along a path traversing the cylindrical surfaces (10, 12).

3. A joint according to claim 2 wherein the setting device (20) comprises a locking screw extending from the pivot point in one of the elements, and received in a threaded sleeve extending from the pivot point in the other of the elements, one of the screw or sleeve being rotatably mounted at its respective pivot point to adjust the length of the device.

4. A joint according to claim 1, including spherical joints at the pivot points in the first and second elements defining respective ends of the setting device.

5. A joint according to claim 1, wherein the second element comprises a block defining the female cylindrical surface, and a sleeve surrounding the block and defining the fulcrum, the block being fixedly securable in the sleeve.

6. A hip compression screw assembly comprising an adjustable joint, comprising first and second elements formed with complementary male and female cylindrical surfaces defining the plane of adjustment, the first element defining a hinge point at the axis of the male cylindrical surface and the second element including a fulcrum extending to the axis of the female cylindrical surface, and a setting device extending between pivot points on the first and second elements and adjustable in length to alter the angle between the elements, wherein the first element is adapted to lay against a section of a femur with the hinge point at the edge of a hole in the femur for receiving a lag screw, the second element comprises the lag screw for securement in a caput of the femur; and, wherein the adjustable joint is constrained to pivotal movement in a single two-dimensional plane.

7. A method of treating a proximal femur fracture using a hip compressor screw assembly comprising a joint adjustable in two dimensions, comprising first and second elements formed with complementary male and female cylindrical surfaces defining the plane of adjustment, the first element defining a hinge point at the axis of the male cylindrical surface and the second element including a fulcrum extending to the axis of the female cylindrical surface, and a setting device extending between pivot points on the first and second elements and adjustable in length to alter the angle between the elements, wherein the first element is adapted to lay against a section of femur with the hinge point at the edge of a hole in the femur for receiving a lag screw, the second element comprises the lag screw for securement in a caput of the femur, the method comprising securing the lag screw in the caput with the hinge point on the first element at the surface of the femur, adjusting the setting device to orient the first element of the joint on the femur surface; and securing the first element to the femur.

8. An adjustable joint for the external fixation of a limb comprising first and second elements formed with complementary male and female cylindrical surfaces defining the plane of adjustment, the first element defining a hinge point at the axis of the male cylindrical surface and the second element including a fulcrum extending to the axis of the female cylindrical surface, and a setting device extending between pivot points on the first and second elements and adjustable in length to alter the angle between the elements, wherein the first element is adapted to lay against a section of femur with the hinge point at the edge of a hole in the femur for receiving a lag screw, the second element comprises the lag screw for securement in a caput of the femur, wherein the first and second elements are attached to limb sections to be fixed, and the setting device being adjusted to establish the desired orientation thereof; and, wherein the adjustable joint is constrained to pivotal movement in a single two-dimensional plane.

* * * * *